United States Patent [19]

Kwon et al.

[11] 4,450,407

[45] May 22, 1984

[54] MAGNETIC RESONANCE CELL AND METHOD FOR ITS FABRICATION

[75] Inventors: Tae M. Kwon, Thousand Oaks; William P. Debley, Sepulveda, both of Calif.

[73] Assignee: Litton Systems, Inc., Beverly Hills, Calif.

[21] Appl. No.: 307,995

[22] Filed: Oct. 2, 1981

[51] Int. Cl.³ .......................................... G01R 33/08
[52] U.S. Cl. .................................... 324/304; 324/300
[58] Field of Search ................ 324/300, 304, 305, 301

[56] References Cited

U.S. PATENT DOCUMENTS

| | | | |
|---|---|---|---|
| 3,165,705 | 1/1965 | Dicke | 324/304 |
| 3,252,081 | 5/1966 | Ruddock | 324/304 |
| 3,267,360 | 8/1966 | Dehmelt | 324/304 |
| 3,500,176 | 3/1970 | Kastler | 324/304 |
| 3,652,926 | 3/1972 | Brun | 324/304 |
| 4,005,355 | 1/1977 | Happer | 324/304 |

Primary Examiner—Michael J. Tokar
Attorney, Agent, or Firm—G. L. Cline

[57] ABSTRACT

There is disclosed a magnetic alignment device and method for its fabrication in which the aligned magnetic moments of a gas enclosed within a container have an increased relaxation time, hence an increase signal to noise output.

One embodiment is a nuclear magnetic resonance gyroscope including a container for gas having a layer of rubidium hydride on its inner surface. Enclosed within the container is rubidium vapor and xenon-131 gas.

The layer of rubidium hydride is manufactured by reacting hydrogen gas and rubidium at a temperature between approximately 70° and about 250° C. In one specific method, a layer of rubidium hydride is formed by heating rubidium and hydrogen gas at about 85° for about 7 days.

62 Claims, 3 Drawing Figures

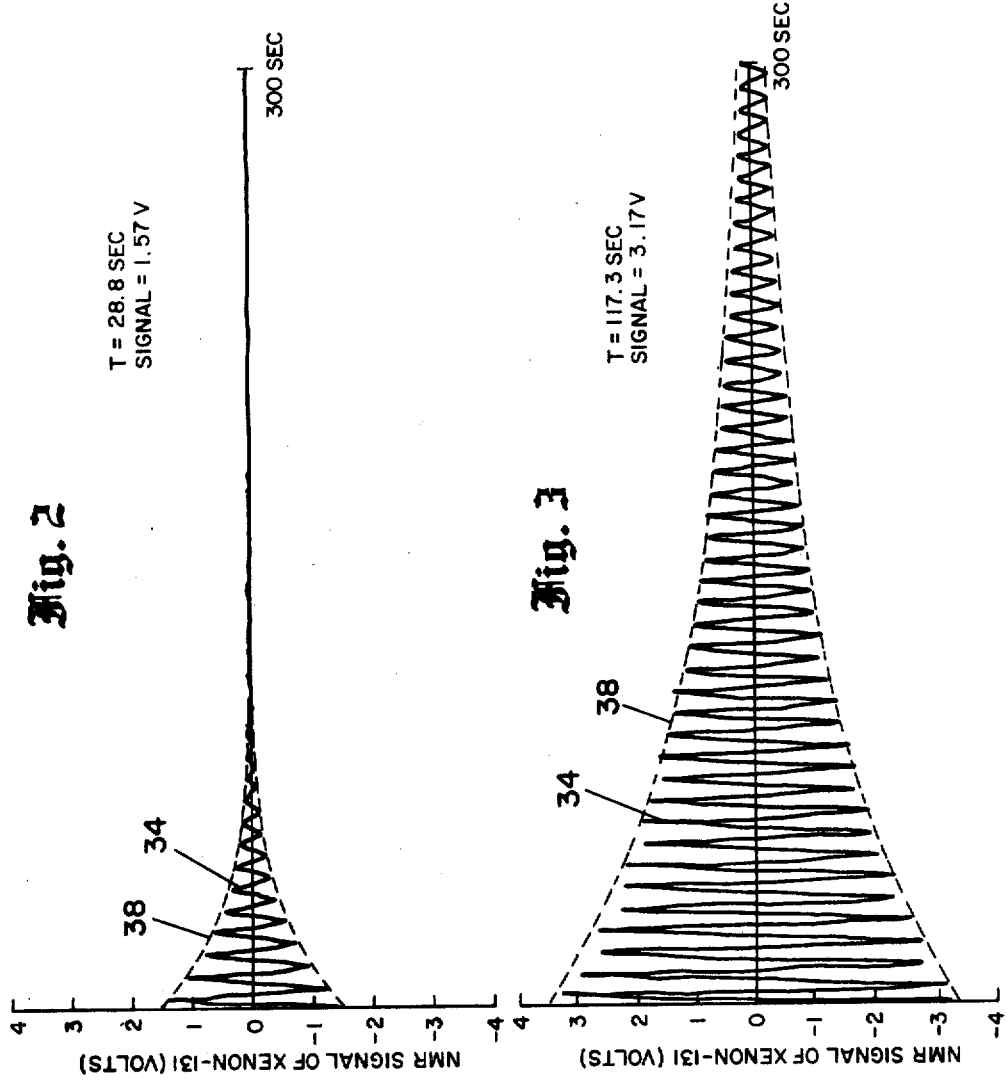

MAGNETIC RESONANCE CELL AND METHOD FOR ITS FABRICATION

The Government has rights in this invention pursuant to Contract No. F49620-77-C-0047 awarded by the Air Force Office of Scientific Research.

TECHNICAL FIELD

This invention relates generally to the creation and detection of atomic and nuclear magnetic resonance. More particularly, this invention relates to magnetic resonance devices having aligned magnetic moment gases contained in a cell.

BACKGROUND ART

The present invention is directed to a magnetic resonance device with a gas container having an alkali metal hydride coating on the inner surface of the cell. The use of a container having its rotationally symmetric axis oriented at a given angle to the magnetic field, the container enclosing at least one magnetic moment gas having a nuclear electric quadruple moment, included here as part of the preferred embodiment of the invention, is the subject of a separate patent application, GCD 80-27-B, filed by T. M. Kwon and C. H. Volk, concurrently with the present application.

Magnetic resonance phenomena are well understood by those of ordinary skill in the art and a variety of its practical applications in the science and engineering fields are readily available. For the purposes of this discussion, magnetic resonance includes both atomic magnetic resonance and nuclear magnetic resonance.

One particular and important application of the invention to be described is to a nuclear magnetic resonance (hereinafter refered to as NMR) angular rate sensor or gyroscope. U.S. Pat. No. 4,157,495, hereby incorporated by reference into this document, discloses a NMR gyroscope that operates on the principle of sensing inertial angular rotation rate or angular displacement about a sensitive axis of the device as a shift in the Larmor precession frequency or phase, respectively, of one or more isotopes that possess nuclear magnetic moments.

The gyroscope is composed of an angular rotation sensor and associated electronics. The principal elements of the sensor are a light source, an NMR cell, a photodetector, a set of magnetic shields and a set of magnetic field coils. The principal elements of the elctronics are signal processing circuits for extracting the Larmor precession frequency and phase information as well as circuits for generating and controlling various magnetic fields, both steady and varying sinusoidally with time, that are necessary for the proper operation of the device.

The NMR cell is mounted within a set of magnetic shields in order to attenuate external magnetic fields to acceptable low levels. Magnetic field coils are used to apply very uniform magnetic fields to the NMR cell. Both a steady field and an ac carrier field are applied along the sensitive axis of the device and AC feedback fields are applied along one of the transverse axes. The DC magnetic fields along both transverse axes are controlled to be substantially zero. The NMR cell contains a single alkali metal vapor, such as rubidium, together with two isotopes of one or more noble gases, such as krypton-83, and xenon-129, or xenon-131. One or more buffer gases such as helium and nitrogen may also be contained in the cell. The NMR cell is illuminated by a beam of circularly polarized light that originates from a source such as a rubidium lamp and which passes through the cell at an angle with respect to the steady magnetic field. Absorption of some of this light causes the atomic magnetic moments of the rubidium atoms to be partly aligned in the direction of the steady magnetic field. This alignment is partly transferred to the nuclear magnetic moments of the noble gases, and these moments are caused to precess about the direction of the steady magnetic field, which in turn creats magnetic fields that rotate at the respective Larmor precession frequencies of the two noble gases. These rotating fields modulate the precessional motions of the rubidium magnetic moments, which in turn produce corresponding modulations of the transmitted light, thereby making it possible to optically detect the Larmor precession frequencies of the two noble gases.

The modulations of the light intensity are converted into electrical signals by a photodetector, and these signals are then electronically demodulated and filtered to provide signals at the Larmor precession frequencies of the two noble gases. The difference between the two precession frequencies is used to accurately control the steady magnetic field so that it is constant. One of the noble gas precession frequencies is subtracted from a precision reference frequency. The resulting difference frequency is a measure of the angular rotation rate of the gyroscope. The magnitude of an individual nuclear magnetic moment is extremely small and the natural equilibrium condition is one in which a nearly random orientation of moments exists in an ensemble of atoms. Techniques must be used to orient a significant fraction of these magnetic moments in a single direction so that a macroscopic magnetic moment, and consequently a measureable signal, will be produced.

The aligned magnetic moments of the alkali metal system and of both noble gas systems of atoms are subject to relaxation mechanisms which cause their alignments to decay exponentially with time towards their natural equilibrium condition of random orientation. Each system of moments is characterized by a relaxation time constant which depends on the kinds and quantities of all other constituents and upon the total environment in the NMR cell. The steady state fractional alignment of each system of moments is a function of both the pumping rate and the relaxation time for the system, with larger fractional alignments, hence larger signal amplitudes, being achieved when the relaxation times are also long.

Accordingly, a number of prior art techniques exist to achieve longer relaxation times. In one of the techniques, a suitable amount of a buffer gas such as helium or nitrogen is also contained in the cell in order to reduce the relaxation effects due to interactions of the magnetic moments with the walls of the cell. In another technique, particular isotopes of particular noble gases are chosen as the nuclear magnetic moment gases specifically for their long relaxation times. However, a problem still exists in that certain, otherwise desirable magnetic moment gases have relaxation times too short to provide a practical device.

In an article by D. S. Bayles, I. A. Greenwood, and J. H. Simpson in an unpublished report entitled, "Noise Sources in NMR Oscillators and Relaxation Phenomena in Optically-Pumped Mercury Isotopes", *Final Scientific Report*, Air Force Office of Scientific Research, 1976, it was disclosed that the relaxation time constant of the vapor of mercury-201, a species having a quadrupole nuclear moment, is dependent on the particular angle of orientation of the NMR cell to the externally applied magnetic field. The angle between the cell and the magnetic field which yielded the maximum relaxation time constant was termed the "magic angle", a term which will be used herein.

C. H. Volk, J. G. Mark, and B. C. Grover disclose in an article in Physical Review A, Volume 20, pps. 2381-2389, December, 1979, that this angle-dependent effect was observed for krypton-83, a noble gas also having a nuclear electric quadrupole moment. The magic angle was found experimentally to be an undetermined function of the spatial distribution of the reservoir of rubidium metal spread over the cell. Because of this undetermined dependence of magic angle on distribution of the rubidium metal, the magic angle for a given cell must be empirically determined by a time consuming trial and error approach in which the relaxation time constant is measured at many different angles of cell orientation.

It should be noted that no prior art, including the articles referred to above, disclose or suggest how to define the specific reference axis of the cell which must be aligned to the magnetic field so as to yield the magic angle. In other words, there is nowhere disclosed what axis in the cell is to be taken to determine the magic angle. For example, in the article by Volk, et al, the cell axis is arbitrarily defined as "a line that passes symmetrically through the tip off region of the cell *as a matter of convenience*" (italics supplied for emphasis).

SUMMARY OF THE INVENTION

Accordingly, it is an object of the present invention to provide a magnetic alignment device in which the aligned magnetic moments of a gas enclosed within a container have an increased relaxation time.

Another object of the invention is to provide a method for fabricating such a container.

These and other objects and advantages are accomplished in a cell for use in a magnetic alignment device which includes a container for a magnetic moment gas and a layer of alkali metal hydride deposited on the inner surface of the container.

In various embodiments of the invention, the alkali metal component in the layer of alkali metal hydride is selected from the group consisting of cesium, lithium, potassium, sodium, and rubidium. The magnetic moment gases enclosed within the various embodiments of the invention can include xenon-131, xenon-129, krypton-83, mercury-201, cesium, potassium, sodium, and rubidium.

In a specific embodiment of the invention, the cell is used in a nuclear magnetic resonance gyroscope, the layer is rubidium hydride, and among the magnetic moment gases enclosed within the container is rubidium and xenon-131.

An aspect of the invention is a method for manufacturing the layer of alkali metal hydride in which hydrogen gas and an alkali metal is reacted by heating at a temperature between approximately 70 and about 250° C. In one specific method, a layer of rubidium hydride is formed by heating rubidium and hydrogen gas at about 85° for about 7 days.

BRIEF DESCRIPTION OF THE DRAWINGS

These and other objects, advantages, and features will become more fully apparent from the following detailed description of the invention when considered in conjunction with the accompanying drawings.

FIG. 2 shows the relaxation time of xenon-131 contained in a prior art nuclear magnetic resonance cell.

FIG. 3 shows the relaxation time of xenon-131 in a nuclear magnetic resonance cell constructed in accordance with one embodiment of the present invention.

DETAILED DESCRIPTION OF THE DRAWING

Figure 1:
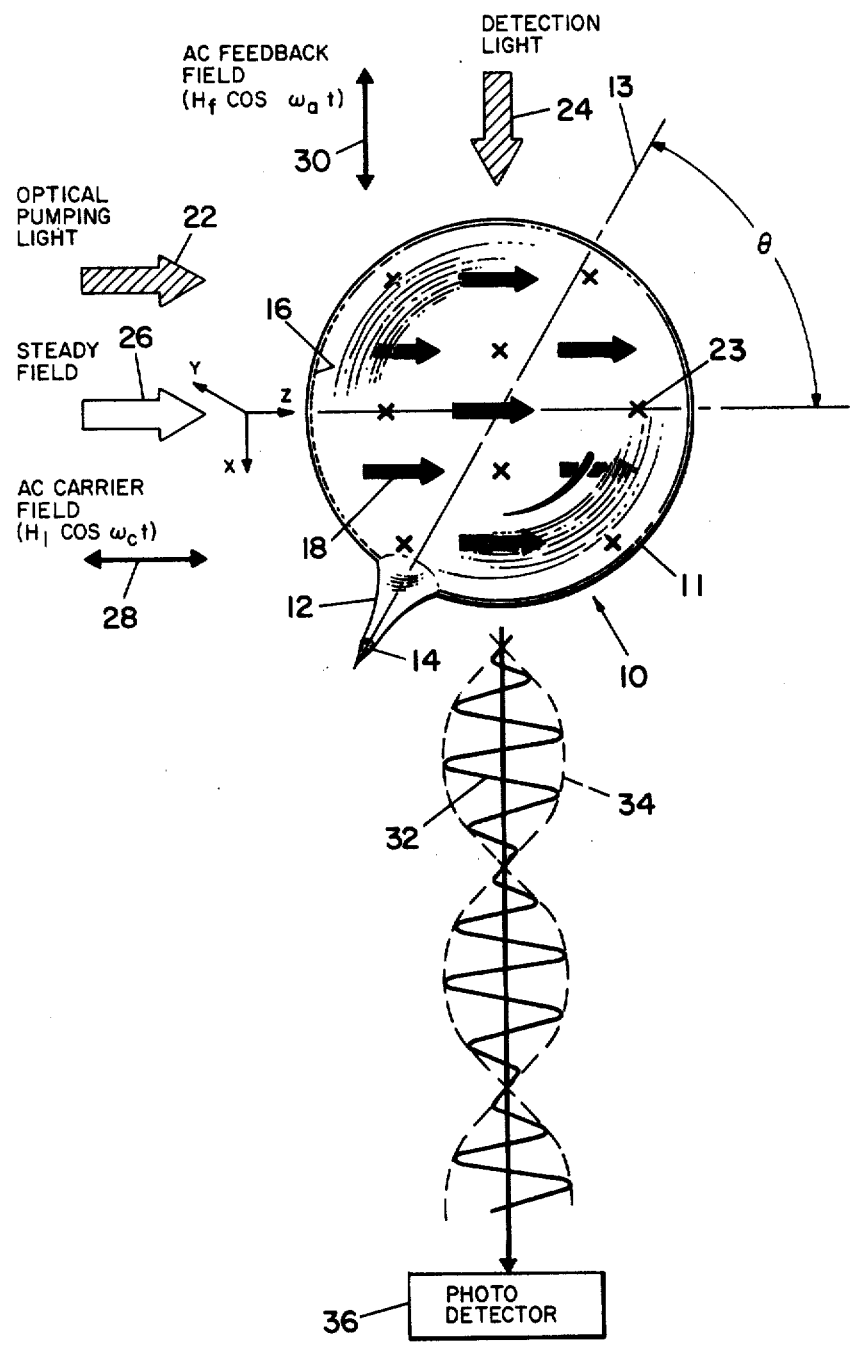
FIG. 1 is a conceptual diagram, adapted from FIG. 3 of U.S. Pat. No. 4,157,495, of an NMR gyro having an NMR cell made in accordance with one embodiment of the present invention.

FIG. 1 is a conceptual diagram illustrating for each of the noble gases the processes of optical pumping and of modulation of the intensity of the light that is transmitted through the NMR cell 10.

The NMR cell 10 is a sealed, optically transparent container for gas which has a shape which is rotationally symmetric about an axis of symmetry 13. In a preferred embodiment, cell 10 includes a spherical portion 11 and a tip portion 12.

The cell 10 is suitably of Pyrex glass and has a volume of approximately one milliliter.

In an illustrative embodiment, the cell contains a small quantity of isotopically enriched rubidium-87 metal, 0.1 Torr xenon-129, 0.4 Torr xenon-131, and a combination of buffer gases consisting of about 10 Torr nitrogen and 100 Torr helium. The cell 10 is filled through tip 12 which is then sealed off as shown.

Some of the rubidium is in the form of a pellet 14 deposited in the tip 12 while the rest is in the form of a vapor. The rubidium pellet 14 serves as a reservoir necessary to replenish the portion of rubidium vapor which gradually and inavoidably disappears from the interior of the cell.

In contrast to the prior art magnetic resonance cells which use an essentially uncontrolled spatial distribution of rubidium, the pellet 14 is disposed within tip 12 such that the pellet is substantially rotationally symmetric to the axis 13. In the specific embodiment of FIG. 1, this symmetry is acheived by having the tip 12 located on axis 13 thereby causing the pellet 14 to settle on axis 13.

The cell is mounted in a temperature controlled oven (not shown) and maintained at a temperature of approximately 80 degrees C., at which temperature rubidium is vaporized from pellet 14 in a quantity sufficient to absorb a substantial fraction of the pumping light entering the cell 10.

The axis 13 of cell 10 is oriented to the steady magnetic field 26 at approximately the magic angle $\theta$, where $\theta$ is defined by the expression $$\theta = \cos^{-1}(\tfrac{1}{3})^{\frac{1}{2}} \approx 55°$$

It should be understood that the magic angle is actually a cone angle in that the axis 13 can be oriented at the magic angle in any arbitrary direction about the steady field 26 to thereby sweep out an imaginary cone having its axis along the field 26. Furthermore, the magic angle is independent of the directional sense of the steady magnetic field 26. Thus, a 180° reversal of magnetic field 26 leaves the magic angle undisturbed.

The orientation and symmetry of the cell described above is in accordance with the discovery that the relaxation time of a magnetic moment gas having a nuclear electric quadrupole moment, such as xenon-131, is increased if the inner surface of the container 10 and pellet 14 each have a co-linear rotational axis of symmetry, such as axis 13, which is aligned at the magic angle to the magnetic field.

Reasoning based on the theory of quantum mechanics indicates that an aligned atom having a nuclear electric quadrupole moment, such as possessed by xenon-131, krypton-83 and mercury-201, is relaxed by the electric field gradients which it experiences during collisions of the atom with the walls of the container. Theory further indicates that when these electric field gradients are rotationally symmetric about an axis which is substantially at the magic angle to the applied magnetic field, then the relaxation time is at a maximum. Such rotational symmetry is provided by a cell whose inner surface has a rotational axis of symmetry such as exists for the container 10 and pellet 14. As was noted previously, the use of such symmetry, although it is part of the preferred embodiment of FIG. 1, forms no part of the invention claimed herein.

In accordance with the invention, a layer 16 of rubidium hybride is deposited on the inner surface of container 10. As will be discussed, it has been discovered that such a film significantly increases the relaxation time constant of the xenon-131 magnetic moments. The increase is additive to the increase gained by the technique for orientation of the axis of symmetry of the NMR cell to the magic angle described previously. In contrast to this magic angle technique which works only for gases with nuclear electric quadrupole moments, the alkali hydride coating increases the relaxation time of magnetic moment gases with or without nuclear electric quadrupole moments.

Because the processes of optical pumping and of modulation of intensity of the light transmitted through cell 10 are so similar for each of the two noble gases, they are illustrated and described for only one of the two noble gases. The circularly polarized light at a preselected wavelength which rubidium absorbs, is from a rubidium vapor lamp. The light which enters the NMR cell 10 through the spherical portion 11 has a component 22 traveling along the z-axis which is referred to as optical pumping light, and a component 24 traveling along the x-axis, which is referred to as detection light. Through the interactions of the optical pumping light 22 and the steady magnetic field 26, the rubidium atoms 18 have their magnetic moments aligned preferentially in the z-direction. By inter-atomic collisions, this magnetic moment alignment is transferred from the rubidium atoms 18 to the noble gas nuclei 23.

A sinusoidal ac feedback magnetic field 30 that is matched in frequency and phase to the Larmor precession frequency of the collective magnetic moment of the noble gas nuclei 23 is applied in the x-direction and serves to torque the magnetic moment of these nuclei to the x-y plane. This component of noble gas nuclear magnetic moment then precesses in the x-y plane at the noble gas Larmor precession frequency $\omega_a$ about the steady magnetic field 26. This precessing nuclear magnetic momentt component creates a nuclear precession magnetic field of strength $h_a$ that rotates in the x-y plane and which therefore has a component in the y-direction that is equal to ($h_a \cos \omega_a t$).

The detection light 24 interacts with the rubidium atoms 18 which are under the influence of the steady magnetic field 26, a superimposed AC carrier magnetic field 28, and the y-component of the nuclear precession field $h_a$. This interaction causes the intensity of the x-component of the transmitted light 32 to be modulated at the carrier frequency, $\omega_a$, with a modulation envelope 34 at the nuclear precession frequency $\omega_a$. These light modulations are then converted into electrical signals by the photodetector 36. The electrical signals may be used by an electronic circuit to create signals which are measures of angular velocity of the gyro as in U.S. Pat. No. 4,157,495.

In order to demonstrate the invention, the relaxation times of aligned nuclear magnetic moments of xenon-131 were experimentally measured for a number of cells made in the same batch, the cells being identical except that some were made with, and the others made without, a coating of rubidium hydride. The experimental apparatus was similar to that of FIG. 1 except that it was operated not as a gyroscope, but rather to specifically measure the relaxation time of xenon-131 by measuring the effective magnetic field $h_a$ generated by the aligned xenon-131. This well known mode of operation is thoroughly discussed in articles by C. Cohen-Tannoudji, J. Dupont-Roc, S. Haroch, and F. Laloe, in *Physical Review Letters*, Volume 22, page 758, 1969; and by the same authors in *Review de Physique Appliquee*, Volume 5, page 102, 1970; and by C. H. Volk, T. M. Kwon, and J. G. Mark in *Physical Review A*, Volume 21, page 1549, 1980.

For sake of completeness of the disclosure, the particular experimental procedures will now be described. The rubidium vapor is optically pumped by illuminating the cell with circularly polarized light from a rubidium discharge lamp at the $D_1$ rubidium spectral line.

In the presence of the pumping light, a 2 milligauss field was applied along the z-axis, for 10 minutes, a time in which a significant fraction of the noble gas magnetic moments are aligned along the z-axis by spin exchange collisions with the optically oriented vapor. The z-field is then switched to zero while a precessional magnetic field of approximately 350 microgauss is applied along the y-axis. An ac magnetic field is simultaneously applied along the x-axis for the purpose of detecting the precessional magnetic field generated by the aligned xenon nuclear magnetic moments.

The y-axis field mentioned above defines the axis about which the cell axis is oriented to yield a magic angle, i.e., the angle at which the maximum relaxation time constant occurs. This maximum was found to occur when the cell axis 13 was oriented at the magic angle of approximately 55° to the y-axis, in excellent agreement with the theoretical valve of 55°. The relaxation time constant was not significantly decreased by changing the cell angle by approximately plus and minus 5° away from 55°.

FIGS. 2 and 3 show the typical results of these experiments. In both figures the horizontal axis represents time and the vertical axis represents the response of the silicon photodetector 36 to the x-component of the transmitted light 32. The sinusoidal signal 34 is the modulation envelope of the x-component of the transmitted light. The envelope 38 of the signal 34 yields the relaxation time constant. As shown in FIG. 2, the cell without the rubidium hybrid coating has a relaxation time of 28.8 seconds. This is significantly shorter than for the coated cell of FIG. 3 which has a relaxation time constant of 117.3 seconds. The signal amplitudes of FIGS. 2 and 3 are 1.57 volts and 3.17 volts, respectively, thereby indicating an improvement in signal to noise ratio of over a factor 2 for the coated cell with respect to the uncoated cell. This increased signal is a direct result of the increased relaxation time.

With the axis 13 of container 10 set at the magic angle, it was found that relaxation of the aligned xenon-131 took place in a very short time, when the rubidium reservoir was distributed non-uniformly over the inner surface of container 10, as in the prior art, rather than spatially concentrated as in the pellet 14 in tip 12. In fact, this prior art distribution caused complete relaxation to take place in a few periods of the precession signal 34, a time far too short for a practical device.

With the pellet 14 located on axis 13, the magic angle occurred much more often at the theoretically predicted 55 degrees in those cells having a layer of rubidium hydride than for those without the layer. For example, in a typical batch of 20 cells having the layer of rubidium hydride, approximately 85% had their magic angle substantially at 55 degrees. This was in contrast to another batch of 100 cells made without a layer of rubidium hydride in which only 15% had magic angles substantially at 55 degrees.

A further advantage of combining the rubidium hydride coating with the symmetrical cell is the fact that cells having a magic angle of 55 degrees rather than some other angle exhibited a larger precessional signal 34 than cells having some other magic angle.

Although the reasons for the beneficial effects of rubidium hydride coatings on a nuclear magnetic resonance cell are not completely understood, theoretical work has been carried out which leads to the following highly tentative physical picture. The rubidium hydride covers microscopic impurities non-uniformly located on the inner surface of the container that, unless coated, give rise to electric field gradients at the walls. These gradients produce strong relaxation forces upon the aligned moments of the gas.

In addition, the non-uniform spatial distribution of the impurities on the wall decreases the symmetry of the field gradients on the inner surface of the cell which, in the case of nuclear electric quadrupole moment gases, is required to reliably produce a magic angle at 55°.

It thus follows that the relaxation time increase is caused, at least in part, by a reduction in field gradients effected by the coating. By reducing the magnitude of the effects of the non-uniformly distributed wall impurities, the coating also produces a greater symmetry of field gradients so that cells with nuclear electric quadrupole moment gases are more likely to have magic angles at 55°.

A further reason for these beneficial effects is believed to be that the coating modifies the absorption energy of the cell walls so as to reduce the sticking time, the time period which an atom colliding with the cell wall remains on the wall prior to rebounding away. This advantageously decreases the time during which the field gradients can act on the colliding atom, thereby decreasing the relaxation effects.

In one particularly suitable method of producing the layer 16 of rubidium hydride on the inner surface of container 10 shown in FIG. 1, the glass container 10 is first connected at the tip 12 to a vacuum gas filling system. After evacuation, the cell 10 is filled with the species and in the amounts previously described with the addition of approximately 10 Torr of hydrogen gas. The rubidium is added in an amount in the excess of a stoich-metric mixture with respect to the hydrogen. The substances can be added in any convenient order. The cell 10 is then sealed, removed from the vacuum gas filling system and then maintained at an elevated temperature for a time period sufficient for the hydrogen and rubidium to react to produce a rubidium hydride coating on the inner surface of the container 10. The presence of the coating manifests itself by a clearly visible milky color on the container walls. The temperature at which the cell is maintained is sufficiently high to form rubidium hydride on the inner walls of cell 10 within a time period short enough to be practical. The temperature is sufficiently low to maintain an unreacted portion of the rubidium metal within the cell. In one embodiment of the method, the temperature was maintained at approximately 85° C. for approximately 7 days. In other embodiments the temperature can be maintained in the range from 70° C. to 90° C. from between 4 to 14 days.

Practical temperatures can range from about 70° C. to about 250° C. At much below the lower temperature, the reaction takes too long to be practical. Much above the higher temperature, it has been determined that the unreacted rubidium metal disappears, probably because of diffusion into or through the cell walls or because of a reaction with the cell walls. An additional short-coming of such a higher temperature is that impurities are driven off the cell walls, resulting in contamination of the gas mixture.

Insofar as known, the method of manufacturing a coating of rubidium hydride described above is novel.

During the heating period, the unreacted rubidium metal is vaporized and re-deposited all over the inner surface of the container 10. After the heating is completed, the spatially dispersed rubidium is re-vaporized and condensed as the pellet 14 positioned in the tip 12 by the well known technique of gently heating the 10 cell with a flame while holding the tip 12 in cool water so as to maintain the tip 12 cooler than the cell walls.

One prior art method for making rubidium hydride consists of heating a mixture of rubidium and hydrogen a temperature range between 400 and 600 degrees C. As described above, such high temperature range would cause problems of making rubidium hydride coatings in a closed system. However, it could be used to make the coating in cells which were then cooled prior to adding excess rubidium and other gases.

Another known method of manufacturing rubidium hydride consists of reacting a mixture of rubidium and hydrogen by subjecting the mixture to a high intensity light source, such as a laser, at the wavelength corresponding to the resonance radiation line of rubidium. Although such a method might produce useable coatings, it is more expensive than the method of the invention because of the need for a high power laser.

Although the invention has been described with reference to a particular embodiment, numerous modifications will be obvious to those schooled in the art. Therefore it is intended that such modifications shall lie within the scope of the invention as claimed in the following claims.

For example, it is expected that the beneficial effects of rubidium hybride are shared by other alkali metal hydrides including hydrides of cesium, potassium, sodium and lithium.

A coating of either rubidium hydride or other alkali metal hydride is expected to increase the relaxation time constant for many gases and vapors which exhibit magnetic moments. Such gases include the noble gases krypton-83, krypton-85 neon-21, xenon-129, and helium-3, as well as the alkali metal vapors, in particular, rubidium, cesium, and sodium, Mercury-199 and mercury-201, vapors of which are also used in magnetic resonance cells, should also have their relaxation times extended by an alkali metal hydride coating on the cell wall.

It should be pointed out that the greatest benefit of the alkali metal coating is to be gained from those gases which have a particularly strong interaction with the wall. It is well known that these interactions are strongest with the magnetic moment gases which possess nuclear quadrupole moments. Examples of species with nuclear quadrupole moments are xenon-131, neon-21, krypton-83 and mercury-201.

The scope of the invention extends to gas containers for magnetic moment gases which are made from materials other than glass, including quartz, fused silica, sapphire, and similar smooth walled containers.

It will further be obvious to those of ordinary skill in the art that the advantageous properties of an alkali metal hydride layer of the invention could be used not only in a NMR gyroscopes, but also in cells used in other types of magnetic resonance devices such as alkali vapor frequency standards, for example, a rubidium frequency standard, as well as in alkali vapor magnetometers, and also in magnetic resonance apparatus for studying the interaction of magnetic moment gases with container walls.

What is claimed is:

1. A process for treating the inner surface of a magnetic moment gas container to increase the relaxation time constant of aligned magnetic moments of at least one magnetic moment gas contained within, comprising:
   (a) coating said inner surface of said magnetic moment gas container with an alkali metal hydride; and
   (b) introducing into said container at least one magnetic moment gas selected from the group consisting of xenon-131 and krypton-83.

2. A process for treating the inner surface of a magnetic moment gas container to increase the relaxation time constant of aligned magnetic moments of at least one magnetic moment gas contained within, comprising:
   (a) coating said inner surface of said magnetic moment gas container with an alkali metal hydride where the alkali metal is selected from the group consisting of lithium, cesium, potassium, sodium and rubidium; and
   (b) introducing into said container at least one magnetic moment gas selected from the group consisting of xenon-131 and krypton-83.

3. A process for treating the inner surface of a magnetic moment gas container to increase the relaxation time constant of aligned magnetic moments of at least one magnetic moment gas contained within, comprising:
   (a) coating said inner surface of said magnetic moment gas container with an alkali metal hydride where the alkali metal is selected from the group consisting of cesium, sodium and rubidium; and
   (b) introducing into said container at least one magnetic moment gas selected from the group consisting of xenon-141 and krypton-83.

4. A process for treating the inner surface of a magnetic moment gas container to increase the relaxation time constant of aligned magnetic moments of at least one magnetic moment gas contained within, comprising:
   (a) coating said inner surface of said magnetic moment gas container with rubidium hydride; and
   (b) introducing into said container at least one magnetic moment gas selected from the group consisting of xenon-131 and krypton-83.

5. A process for treating the inner surface of a magnetic moment gas container to increase the relaxation time of aligned magnetic moments of a nuclear quadrupole moment gas contained within, comprising:
   (a) coating said inner surface of said magnetic moment gas container with an alkali metal hydride where the alkali metal is selected from the group consisting of cesium, potassium, sodium, and rubidium; and
   (b) introducing into said container at least one magnetic moment gas selected from the group consisting of xenon-131 and krypton-83.

6. A process for treating the inner surface of a magnetic moment gas container to increase the relaxation time of aligned magnetic moments of at least one magnetic moment gas contained within, comprising:
   (a) coating said inner surface of said magnetic moment gas container with rubidium hydride; and
   (b) introducing into said container Xenon-131 gas.

7. A process for increasing the relaxation time of aligned magnetic moments of at least one magnetic moment gas comprising:
   (a) providing a magnetic moment gas container made from a material selected from the group consisting of glass, fused silica, quartz and sapphire;
   (b) reacting hydrogen gas with an alkali metal selected from the group comprising cesium, potassium, rubidium and sodium to deposit a layer of alkali metal hydride on the inner surface of said container; and
   (c) introducing into said container at least one magnetic moment gas selected from the group consisting of xenon-131 and krypton-83.

8. A method of manufacturing alkali metal hydride comprising:
   (a) reacting, in a closed container, hydrogen with an alkali metal selected from the group consisting of cesium, potassium, sodium, and rubidium, said alkali metal being in excess of stoichiometric, at a temperature sufficiently high to form the corresponding metal hydride on the inner walls of said container, and sufficiently low so as to maintain 9 within said container the presence of an unreacted portion 10 of said alkali metal; and
   (b) introducing into said container at least one magnetic moment gas selected from the group consisting of xenon-131 and krypton-83.

9. The method of claim 8 wherein the temperature is from about 70 degrees C. and to about 250 degrees C.

10. The method of claim 8 wherein the temperature is maintained within the range from about 70 degrees C. to 90 degrees C. for about four to about fourteen days.

11. The method of either of claims 8 through 10 wherein said container is of a material selected from the group consisting of glass, quartz, fused silica, and sapphire.

12. The method of claim 8 wherein the temperature is maintained until said walls of said container appear milky white.

13. A method for treating a container for gas comprising:
   (a) evacuating said container;

(b) introducing into said container a predetermined quantity of hydrogen gas;

(c) introducing into said container a predetermined amount of rubidium;

(d) introducing into said container a predetermined amount of xenon-131; and (e) heating said container in the presence of said hydrogen and xenon gases and said rubidium to a temperature between about 70 degrees C. and less than about 400 degrees C. for a time sufficient to deposit a film of rubidium hydride on the inner walls of said container.

14. The method of claim 13 further comprising sealing the container after completing steps (a) through (d) and prior to beginning step (e).

15. The method of claim 13 wherein said temperature is about 70 degrees C. to 90 degrees C.

16. The method of claim 15 wherein said temperature is maintained from about five to nine days.

17. The method of claim 16 wherein said temperature is maintained at about 85° for about 7 days.

18. The method of claim 13 wherein said predetermined quantity of said hydrogen gas is a partial pressure from about three to ten Torr at conditions of standard temperature and pressure and the volume of said container is from about one half to three milliliters.

19. The method of claim 13 wherein said predetermined quantity of said alkali metal is at least stoichiometric with respect to said hydrogen gas.

20. A cell for use in a magnetic alignment device comprising:

(a) a glass container for gas;

(b) a layer of rubidium hydride deposited on the inner walls of said container; and (c) rubidium vapor in said container.

21. A cell for use in a magnetic alignment device comprising:

(a) a glass container for gas;

(b) a layer of rubidium hydride on the inner walls of said container;

(c) rubidium vapor in said container;

(d) xenon-131 gas in said container.

22. A nuclear magnetic resonance detection device comprising:

(a) a container for gas;

(b) at least one optically pumpable substance, selected from the group consisting of cesium, potassium, sodium, and rubidium, said pumpable substance being contained in said cell;

(c) at least one nuclear moment gas selected from the group comprising xenon-131 and krypton-83 also contained within said cell, the nuclear magnetic moments of each of said at least one nuclear moment gases being capable of being at least partially aligned;

(d) means for applying a steady magnetic field to said cell;

(e) first means for illuminating said cell with pumping light capable of partially aligning the magnetic moments of said optically pumpable substance in one direction;

(f) means for precessing said nuclear magnetic moments of said at least one nuclear moment gas about the direction of the steady magnetic field at the respective Larmor precession frequencies of said at least one nuclear moment gas;

(g) means for applying an AC carrier magnetic field to said cell; and (h) a layer of alkali metal hydride deposited on the inner wall of said container, said alkali metal being selected from the group consisting of cesium, potassium, sodium, and rubidium.

23. The device of claim 22 wherein said alkali metal hydride is rubidium hydride.

24. The device of claim 23 in which said at least one nuclear moment gas is xenon-131.

25. The device of claims 22, 23, or 24 in which said at least one optically pumpable substance is rubidium vapor.

26. The device of claims 22, 23, or 24 in which said container is glass.

27. The device of claim 25 in which said container is glass.

28. A process for treating the inner surface of a container for gas to increase the relaxation time constant of aligned magnetic moments of at least one magnetic moment gas contained within, comprising:

(a) coating said inner surface of said container with rubidium hydride; and (b) introducing into said container at least one magnetic moment gas selected from the group consisting of xenon-131, xenon-129, neon-21, krypton-85, mercury-201, cesium, sodium, and rubidium.

29. A process for increasing the relaxation time of aligned magnetic moments of at least one magnetic moment gas comprising:

(a) providing a gas container made from a material selected from the group consisting of glass, fused silica, quartz and sapphire;

(b) reacting hydrogen gas with an alkali metal selected from the group comprising cesium, potassium, rubidium and sodium to deposit a layer of alkali metal hydride on the inner surface of said container; and (c) introducing into said container at least one magnetic moment gas selected from the group consisting of xenon-131, xenon-129, neon-21, krypton-83, krypton-85, mercury-201, cesium, sodium, and rubidium.

30. A process for treating the inner surface of a container for gas to increase the relaxation time constant of aligned magnetic moments of at least one magnetic moment gas contained within, comprising:

(a) coating said inner surface of said container with rubidium hydride; and (b) introducing into said container at least one magnetic moment gas selected from the group consisting of xenon-131, krypton-83, rubidium, cesium, potassium and sodium.

31. A process for increasing the relaxation time of aligned magnetic moments of at least one magnetic moment gas comprising:

(a) providing a gas container made from a material selected from the group consisting of glass, fused silica, quartz and sapphire;

(b) reacting hydrogen gas with an alkali metal selected from the group comprising cesium, potassium, rubidium and sodium to deposit a layer of alkali metal hydride on the inner surface of said container; and (c) introducing into said container at least one magnetic moment gas selected from the group consisting of xenon-131, krypton-83, rubidium, cesium, potassium and sodium.

32. A process for treating the inner surface of a container for gas to increase the relaxation time constant of aligned magnetic moments of at least one magnetic moment gas contained within, comprising:
 (a) coating said inner surface of said container with rubidium hydride; and
 (b) introducing into said container at least one magnetic moment gas selected from the group consisting of xenon-131, krypton-83, krypton-85, neon-21, and mercury-201.

33. A process for increasing the relaxation time of aligned magnetic moments of at least one magnetic moment gas comprising:
 (a) providing a gas container made from a material selected from the group consisting of glass, fused silica, quartz and sapphire;
 (b) reacting hydrogen gas with an alkali metal selected from the group comprising cesium, potassium, rubidium and sodium to deposit a layer of alkali metal hydride on the inner surface of said container; and
 (c) introducing into said container at least one magnetic moment gas selected from the group consisting of xenon-131, krypton-83, krypton-85, neon-21, and mercury-201.

34. A method for manufacturing a cell for use in magnetic alignment devices comprising:
 (a) evacuating a container;
 (b) introducing into said container a predetermined quantity of hydrogen gas;
 (c) introducing into said container a predetermined quantity of an alkali metal selected from the group consisting of cesium, potassium, sodium, and rubidium;
 (d) heating said container in the presence of said hydrogen gas and said alkali metal to a temperature between about 70 degrees C. and about 250 degrees C. for a time sufficient to form alkali metal hydride on the inner walls of said container; and
 (e) introducing into said container at least one magnetic moment gas selected from the group consisting of krypton-83, krypton-85, xenon-131, xenon-129, neon-21, mercury-201, cesium, potassium, sodium and rubidium.

35. A method for manufacturing a cell for use in magnetic alignment devices comprising:
 (a) evacuating a container;
 (b) introducing into said container a predetermined quantity of hydrogen gas;
 (c) introducing into said container a predetermined quantity of an alkali metal selected from the group consisting of cesium, potassium, sodium, and rubidium;
 (d) heating said container in the presence of said hydrogen gas and said alkali metal to a temperature between about 70 degrees C. and about 250 degrees C. for a time sufficient to form alkali metal hydride on the inner walls of said container; and
 (e) introducing into said container at least one magnetic moment gas selected from the group consisting of krypton-85, xenon-131, krypton-83, cesium, potassium, sodium and rubidium.

36. A method for manufacturing a cell for use in magnetic alignment devices comprising:
 (a) evacuating a container;
 (b) introducing into said container a predetermined quantity of hydrogen gas;
 (c) introducing into said container a predetermined quantity of an alkali metal selected from the group consisting of cesium, potassium, sodium, and rubidium;
 (d) heating said container in the presence of said hydrogen gas and said alkali metal to a temperature between about 70 degrees C. and about 250 degrees C. for a time sufficient to form alkali metal hydride on the inner walls of said container; and
 (e) introducing into said container mercury-201 gas.

37. A method for manufacturing a cell for use in magnetic alignment devices comprising:
 (a) evacuating a container;
 (b) introducing into said container a predetermined quantity of hydrogen gas;
 (c) introducing into said container a predetermined quantity of an alkali metal selected from the group consisting of cesium, potassium, sodium, and rubidium;
 (d) heating said container in the presence of said hydrogen gas and said alkali metal to a temperature between about 70 degrees C. and about 250 degrees C. for a time sufficient to form alkali metal hydride on the inner walls of said container; and
 (e) introducing into said container at least one magnetic moment gas selected from the group consisting of xenon-131 and krypton-83.

38. A cell for use in a magnetic alignment device comprising:
 (a) a magnetic moment gas container;
 (b) a layer of alkali metal hydride deposited on the inner wall of said container; and
 (c) within said container at least one gas having a magnetic moment selected from the group comprising xenon-131, neon-21, xenon-129, krypton-83, mercury-199, mercury-201, cesium, potassium, sodium and rubidium.

39. A cell for use in magnetic alignment devices comprising:
 (a) a magnetic moment gas container;
 (b) a layer of alkali metal hydride deposited on the inner wall of the said container, where said alkali metal is selected from the group consisting of cesium, lithium, and potassium, sodium and rubidium; and
 (c) within said container at least one gas having a magnetic moment selected from the group comprising xenon-131, neon-21, xenon-129, krypton-83, mercury-199, mercury-201, cesium, potassium, sodium and rubidium.

40. A cell for use in a magnetic alignment device comprising:
 (a) a magnetic moment gas container;
 (b) a layer of alkali metal hydride deposited on the inner wall of the said container, where said alkali metal is selected from the group consisting of cesium, potassium, sodium, and rubidium; and
 (c) within said container at least one gas having a magnetic moment selected from the group comprising xenon-131, neon-21, xenon-129, krypton-83, mercury-199, mercury-201, cesium, potassium, sodium and rubidium.

41. A cell for use in a magnetic alignment device comprising:
 (a) a magnetic moment gas container;
 (b) a layer of rubidium hydride deposited on the inner wall of said container; and
 (c) within said container at least one gas having a magnetic moment selected from the group comprising xenon-131, neon-21, xenon-129, krypton-83, mercury-199, mercury-201, cesium, potassium, sodium and rubidium.

42. A cell for use in a magnetic alignment device comprising:
(a) a magnetic moment gas container;
(b) a layer of alkali metal hydride deposited on the inner wall of said container; and
(c) within said container at least one gas having a magnetic moment selected from the group consisting of xenon-131, krypton-83, mercury-201, cesium, sodium and rubidium.

43. A cell for use in magnetic alignment devices comprising:
(a) a magnetic moment gas container;
(b) a layer of alkali metal hydride deposited on the inner wall of the said container, where said alkali metal is selected from the group consisting of cesium, lithium, and potassium, sodium and rubidium; and
(c) within said container at least one gas having a magnetic moment selected from the group consisting of xenon-131, krypton-83, mercury-201, cesium, sodium and rubidium.

44. A cell for use in a magnetic alignment device comprising:
(a) a magnetic moment gas container;
(b) a layer of alkali metal hydride deposited on the inner wall of the said container, where said alkali metal is selected from the group consisting of cesium, potassium, sodium, and rubidium; and
(c) within said container at least one gas having a magnetic moment selected from the group consisting of xenon-131, krypton-83, mercury-201, cesium, sodium and rubidium.

45. A cell for use in a magnetic alignment device comprising:
(a) a magnetic moment gas container;
(b) a layer of rubidium hydride deposited on the inner wall of said container; and
(c) within said container at least one gas having a magnetic moment selected from the group consisting of xenon-131, krypton-83, mercury-201, cesium, sodium and rubidium.

46. A cell for use in a magnetic alignment device comprising:
(a) a magnetic moment gas container;
(b) a layer of alkali metal hydride deposited on the inner wall of said container; and
(c) within said container at least one magnetic moment gas selected from the group consisting of xenon-131, krypton-83, krypton-85, neon-21, cesium, potassium, sodium and rubidium.

47. A cell for use in magnetic alignment devices comprising:
(a) a magnetic moment gas container;
(b) a layer of alkali metal hydride deposited on the inner wall of the said container, where said alkali metal is selected from the group consisting of cesium, lithium, and potassium, sodium and rubidium; and
(c) within said container at least one magnetic moment gas selected from the group consisting of xenon-131, krypton-83, krypton-85, neon-21, cesium, potassium, sodium and rubidium.

48. A cell for use in a magnetic alignment device comprising:
(a) a magnetic moment gas container;
(b) a layer of alkali metal hydride deposited on the inner wall of the said container, where said alkali metal is selected from the group consisting of cesium, potassium, sodium, and rubidium; and
(c) within said container at least one magnetic moment gas selected from the group consisting of xenon-131, krypton-83, krypton-85, neon-21, cesium, potassium, sodium and rubidium.

49. A cell for use in a magnetic alignment device comprising:
(a) a magnetic moment gas container;
(b) a layer of rubidium hydride deposited on the inner wall of said container; and
(c) within said container at least one magnetic moment gas selected from the group consisting of xenon-131, krypton-83, krypton-85, neon-21, cesium, potassium, sodium and rubidium.

50. A cell for use in a magnetic alignment device comprising:
(a) a magnetic moment gas container;
(b) a layer of alkali metal hydride deposited on the inner wall of said container; and
(c) within said container at least one magnetic moment gas selected from the group consisting of xenon-131, krypton-83, krypton-85, and mercury-201.

51. A cell for use in magnetic alignment devices comprising:
(a) a magnetic moment gas container;
(b) a layer of alkali metal hydride deposited on the inner wall of the said container, where said alkali metal is selected from the group consisting of cesium, lithium, and potassium, sodium and rubidium; and
(c) within said container at least one magnetic moment gas selected from the group consisting of xenon-131, krypton-83, krypton-85, and mercury-201.

52. A cell for use in a magnetic alignment device comprising:
(a) a magnetic moment gas container;
(b) a layer of alkali metal hydride deposited on the inner wall of the said container, where said alkali metal is selected from the group consisting of cesium, potassium, sodium, and rubidium; and
(c) within said container at least one magnetic moment gas selected from the group consisting of xenon-131, krypton-83, krypton-85, and mercury-201.

53. A cell for use in a magnetic alignment device comprising:
(a) a magnetic moment gas container;
(b) a layer of rubidium hydride deposited on the inner wall of said container; and
(c) within said container at least one magnetic moment gas selected from the group consisting of xenon-131, krypton-83, krypton-85, and mercury-201.

54. A cell for use in a magnetic alignment device comprising:
(a) a magnetic moment gas container;
(b) a layer of alkali metal hydride deposited on the inner wall of said container; and
(c) within said container at least one magnetic moment gas selected from the group consisting of xenon-131 and krypton-83.

55. A cell for use in magnetic alignment devices comprising:

(a) a magnetic moment gas container;
(b) a layer of alkali metal hydride deposited on the inner wall of the said container, where said alkali metal is selected from the group consisting of cesium, lithium, and potassium, sodium and rubidium; and
(c) within said container at least one magnetic moment gas selected from the group consisting of xenon-131 and krypton-83.

56. A cell for use in a magnetic alignment device comprising:
(a) a magnetic moment gas container;
(b) a layer of alkali metal hydride deposited on the inner wall of the said container, where said alkali metal is selected from the group consisting of cesium, potassium, sodium, and rubidium; and
(c) within said container at least one magnetic moment gas selected from the group consisting of xenon-131 and krypton-83.

57. A cell for use in a magnetic alignment device comprising:
(a) a magnetic moment gas container;
(b) a layer of rubidium hydride deposited on the inner wall of said container; and
(c) within said container at least one magnetic moment gas selected from the group consisting of xenon-131 and krypton-83.

58. A cell for use in a magnetic alignment device comprising:
(a) a magnetic moment gas container;
(b) a layer of alkali metal hydride deposited on the inner wall of said container; and
(c) within said container at least xenon-131 gas.

59. A cell for use in magnetic alignment devices comprising:
(a) a magnetic moment gas container;
(b) a layer of alkali metal hydride deposited on the inner wall of the said container, where said alkali metal is selected from the group consisting of cesium, lithium, and potassium, sodium and rubidium; and
(c) within said container at least xenon-131 gas.

60. A cell for use in a magnetic alignment device comprising:
(a) a magnetic moment gas container;
(b) a layer of alkali metal hydride deposited on the inner wall of the said container, where said alkali metal is selected from the group consisting of cesium, potassium, sodium, and rubidium; and
(c) within said container at least xenon-131 gas.

61. A cell for use in a magnetic alignment device comprising:
(a) a magnetic moment gas container;
(b) a layer of rubidium hydride deposited on the inner wall of said container; and
(c) within said container at least xenon-131 gas.

62. The cell of any of claims 49, 53, 57 or 61 wherein said container is made from a material selected from the group consisting of glass, fused silicon, quartz and sapphire.

* * * * *